United States Patent [19]

Tsuchihashi et al.

[11] 4,051,151

[45] Sept. 27, 1977

[54] THIOPHENE DERIVATIVES AND PROCESS FOR PREPARATION THEREOF

[75] Inventors: Genichi Tsuchihashi, Tama; Katsuyuki Ogura, Sagamihara, both of Japan

[73] Assignee: Sagami Chemical Research Center, Tokyo, Japan

[21] Appl. No.: 651,112

[22] Filed: Jan. 21, 1976

[30] Foreign Application Priority Data

Jan. 23, 1975 Japan .................................. 50-9297
Jan. 27, 1975 Japan .................................. 50-10520
Feb. 3, 1975 Japan .................................. 50-13388
Nov. 25, 1975 Japan .................................. 50-140249

[51] Int. Cl.$^2$ ................ C07D 333/00; C07D 333/12; A61K 31/43; A01N 9/00

[52] U.S. Cl. ................ 260/329 S; 260/332.2 A; 260/332.5; 260/347.2; 260/347.3; 424/271; 424/275; 424/285

[58] Field of Search ................ 260/329.5, 332.5

[56] References Cited

U.S. PATENT DOCUMENTS 3,742,066  6/1973  Tsuchihashi et al. ........... 260/609 R

*Primary Examiner*—James O. Thomas, Jr.
*Assistant Examiner*—A. Siegel
*Attorney, Agent, or Firm*—Wenderoth, Lind & Ponack

[57] ABSTRACT

Commercially advantageous processes for preparing thienylacetic acid, furylacetic acid or alkyl esters of these. Novel thiophene or furan derivatives that can be used as starting materials for preparing the above compounds. Processes for preparing these starting materials are also provided.

7 Claims, No Drawings

THIOPHENE DERIVATIVES AND PROCESS FOR PREPARATION THEREOF

This invention relates to a novel process for preparing thienylacetic acid, furylacetic acid or alkyl esters of these; novel compounds used as starting materials in the above process; and to a process for preparing these novel compounds.

Thienylacetic acid, furylacetic acid or alkyl esters of these expressed by the following formula

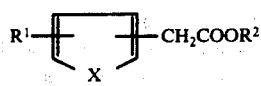   (I)

wherein
X is S or O, and
$R^1$ and $R^2$, independently from each other, represent a hydrogen atom or an alkyl group,
are generally used for organic synthetic reactions, and are especially useful as reagents for chemical modification of antibiotic penicillins and cephalosporins. For example, compounds obtained by bonding thienylacetic acid or furylacetic acid to the 6-amino group of penicillin or the 7-amino group of cephalosporin are known as effective medicines [see E. H. Flynn, "Cephalosporins and Penicillins, Chemistry and Biology," Academic Press, New York, N.Y., 1972, pages 532 – 582, U.S. Pat. No. 3,516,997, and R. R. Chauvette, et al., J. Amer. Chem. Soc., 84, 3401 (1962)].

Conventional processes for preparing heterocyclic-acetic acids or alkyl esters thereof of formula (I), for example, include the following.

1. A process which comprises chloromethylating thiophene, treating the product with sodium cyanide or potassium cyanide to form thienylacetonitrile, and subjecting it to solvolysis with an alkali or acid to form thienylacetic acid or its ester [F. F. Blicke and M. F. Zienty, J. Amer. Chem. Soc., 63, 2945 (1941)].

2. A process which comprises a first step of acetylating thiophene to form methyl 2-thienyl ketone, a second step of heating the ketone together with ammonium polysulfide in an aqueous solution of ammonia to form 2-thienylacetamide, and a third step of hydrolyzing the product to form 2-thienylacetic acid [German Pat. No. 832,755 (1952)].

3. A process which comprises treating thiophenealdehyde or furfural with sodium cyanide and methyl chloroformate to form a compound resulting from the protection of the hydroxyl group of furfural cyanohydrin by a methoxycarbonyl group, then reducing the resulting compound with hydrogen in the presence of a palladium-on-charcoal catalyst to form cyanomethylfuran, and hydrolyzing the product to form thienylacetic acid or furylacetic acid [British Pat. No. 1,122,658].

The process (1), however, requires a precise temperature control in the first-step of chloromethylation, and the yield is as low as 40 to 47%. The alkali cyanide used in the second step is very poisonous, and the operation of the second step is complicated. Moreover, the solvolysis in the third step suffers from a low yield. Thus, this process is very disadvantageous for commercial operations.

The process (2) is also disadvantageous commercially because the yield in the first step is low, heating up to 150° C. is required in the second step, the reaction must be carried out at high temperatures and high pressures, and the reaction in the third step suffers from low yields.

The process (3) is also disadvantageous commercially because sodium cyanide used in the first step is exceedingly poisonous and the operation is complicated, and many reaction steps are required, which in turn may result in reduced yields.

We have made extensive investigations in order to remove the various defects of the conventional processes. Consequently, we found novel compounds of formula (II) shown below which are useful as precursors for the heterocyclic-acetic acids and the alkyl esters thereof expressed by formula (I), and a process for preparation of these compounds, and as a result, a commercially advantageous process for preparing compounds of formula (I) from compounds of formula (II) as starting materials.

The above compounds are derivatives of thiophene or furan expressed by the following formula

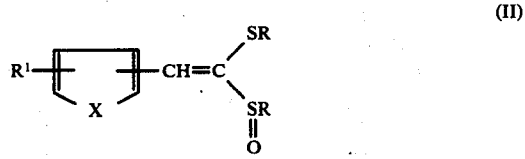   (II)

wherein X and
$R^1$ are the same as defined hereinabove, and
R represents an alkyl or phenyl group which is unsubstituted or substituted.

Preparation of the compounds of formula (II) will be described in detail hereinbelow.

According to the present invention, there is provided a process for preparing thienylacetic acid or furylacetic acid or an alkyl ester of any of these expressed by the following formula

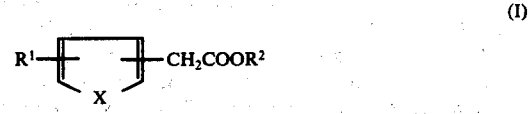   (I)

which comprises reacting a thiophene or furan derivative of the following formula

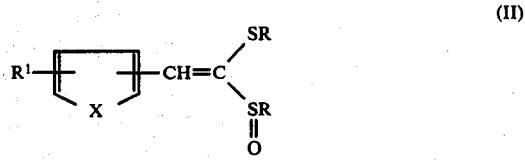   (II)

with water or an alcohol of the formula $R^2OH$   (III)

in the presence of a mineral acid catalyst.

The positions at which the group —$CH_2COOR^2$ and

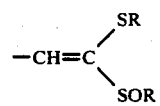

are bonded to the heterocyclic ring in formulae (I) and (II) are any desired positions corresponding to each other. The same can be said with regard to group $R^1$. Furthermore, in these formulae, X is S or O, both of which exhibit almost the same behavior in chemical reactions. $R^1$ represents a hydrogen atom or an alkyl group which is preferably a lower alkyl group with 1 to 4 carbon atoms. $R^2$ represents a hydrogen atom or an alkyl group. The alkyl group is preferably a lower alkyl group with 1 to 5 carbon atoms. The alkyl group means an unsubstituted or substituted alkyl group, and the substituent may, for example, be a halogen atom, a hydroxyl group, and an alkoxy group. Since R does not affect the above reaction, it can generally be any desired group, but preferably an alkyl or phenyl group which is unsubstituted or substituted. The substituent in the substituted alkyl is one which does not directly participate in the reaction, for example, a hydroxyl or alkoxy group. The substituent in the substituted phenyl group is one which does not directly participate in the reaction, for example, alkyl, alkoxy, aryl, nitro and halogen. From the standpoint of commercial availability, R is preferably an alkyl group containing 1 to 5 carbon atoms or a phenyl group.

The mineral acid used as a catalyst in the reaction of forming the compounds of formula (I) is not particularly limited, but from the standpoint of ready availability and the ability to perform the reaction without trouble, hydrogen halides and hydrohalic acids are preferred. Examples of the hydrogen halides and hydrohalic acids are hydrochloric acid. hydrogen chloride, hydrobromic acid, hydrogen bromide, and hydroiodic acid. It is sufficient that the mineral acid is used in a catalytic amount. Specifically, the concentration of the acid in the reation system is preferably at least 0.01 N. Excessively large amounts of the acid are disadvantageous because they will increase the amounts of by-products, and the suitable amount is not more than 12 N.

When the compound of formula (III) is water in the above reaction, thienylacetic acid or furylacetic acid results, and when it is an alcohol, an alkyl ester of thienylacetic acid or furylacetic acid is formed. The reaction components (II) and (III) react in stoichiometric amounts. Generally, however, it is preferred to use the latter in excess because it also serves as a reaction medium. When the reaction component (III) is water, an aprotic solvent such as tetrahydrofuran, diethyl ether, dioxane, methylene chloride, chloroform and benzene can also be used.

The reaction proceeds in good condition at a temperature of $-30°$ C. to 150° C. Usually, temperatures of $-30°$ C. to 100° C. are applied preferably from the standpoint of ready availability.

The reaction product (I) can be isolated from the reaction mixture by conventional means such as distillation, column chromatography or crystallization. When the reaction product (I) is an alkyl ester, it can be hydrolyzed to form the corresponding acid.

In addition to the main product (I), the above reaction usually yields a small amount of a thiol ester of thienylacetic acid or furylacetic acid or the following formula

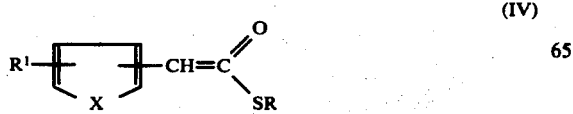
(IV)

wherein
X, $R^1$ and R are the same as defined hereinabove, as a by-product. When this by-product is hydrolyzed, it is converted to a compound of formula (I) in the form of acid, that is, thienylacetic acid or furylacetic acid. Accordingly, when the alkyl ester of formula (I) is prepared using an alcohol as the reaction component (III), the hydrolysis of the reaction mixture containing the thiol ester of formula (IV) results in the conversion of both the main product (I) the by-product (IV) to thienylacetic acid or furylacetic acid. Thus, the yield of such an acid can be increased. This process is therefore also within the scope of the present invention.

The hydrolysis is carried out in the presence of an acid or a base in a manner known per se. The acid is a mineral acid such as hydrochloric acid or sulfuric acid, and the base may be bases generally employed, such as portassium hydroxide, sodium hydroxide, potassium carbonate, sodium carbonate, sodium bicarbonate, and potassium bicarbonate. Hydrolysis with bases is preferred since it permits the reaction to proceed in good condition. The use of solvent is not essential. When a solvent is used, ether-type solvents are preferably used for acid hydrolysis, and alcohol-type or ether-type solvents for base hydrolysis.

Some working examples for illustrating the preparation of thienylacetic acid, furylacetic acid or alkyl esters of these acids expressed by formula (I) will be shown in Examples B-1 to B-18 to be given hereinbelow.

The thiophene or furan derivatives of formula (II) used as one reaction component of the above reaction and their preparation will now be described.

The thiophene or furan derivatives of formula (II) are novel compounds synthesized for the first time by the inventors of the present application.

Accordingly, the present invention also provides a process for preparing novel thiophene or furan derivatives expressed by the following formula

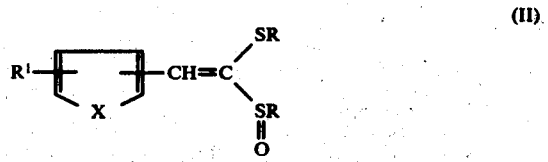
(II)

wherein
X, $R^1$ and R are the same as defined above, which comprises reacting a thiophene or furanaldehyde compound of formula

(V)

wherein
X and $R^1$ are the same as defined hereinabove, with a mercaptal S-oxide of the following formula

(VI)

wherein R is the same as defined above, in the presence of a strongly basic catalyst.

The reaction components (V) and (VI) react in stoichiometrical amounts, but either one of them can be used in excess. The aldehyde compounds of formula (V) are known compounds, and for example, can be prepared almost quantitatively by reacting thiophene or furan with a formamide derivative such as dimethylformamide and phosphorus oxychloride. The mercaptal S-oxides of formula (VI) are compounds develped by the inventors of the present application, and can be easily prepared by the process invented by the inventors of the present application (see, for example, U.S. Pat. No. 3,742,066, German Pat. No. 2,130,923, British Pat. No. 1,401,598, and French Pat. No. 2,193,011).

The strong base used as catalyst has a pH of at least 10 in a 0.1 N aqueous solution. Examples of the strong base are alkali or akaline earth metal hydrides such as sodium hydride or calcium hydride, alkyl lithiums such as butyl lithium, alkali metal amides such as lithium diethylamide, alaki or akaline earth metal alkoxides such as sodium methoxide or magnesium methoxide, alkali or alkaline earth metal hydroxides such as sodium hydroxide or calcium hydroxide, alkaline earth metal oxides such as calcium oxide, quaternary ammonium hydroxides such as trimethylbenzylammonium hydroxide, and alkali metal carbonates such as sodium carbonate. Since the strong base is not consumed in the reaction but acts as a catalyst, its amount can be small. For practical purposes, the amount is at least 0.01 equivalent, preferably at least 0.05 equivalent, based on either one of the reaction materials. The reaction is promoted with increasing amount of the strong base.

The use of solvent is not essential, but if desired, a substance that does not directly participate in the reaction (namely, a substance that does not react with the reaction materials, the product and the base) can be used as a solvent. Examples of such a substance are ordinary organic solvents such as methanol, ethanol, tetrahydrofuran, dioxane, dimethylformamide, and benzene. The reaction proceeds without trouble at room temperature to 150° C., and afford the desired product in a substantially quantitative yield.

Following this reaction, a reaction for forming the compounds of formula (I) can be carried out. Specifically, thienylacetic acid, furylacetic acid or an alkyl ester of each of these acids expressed by formula (I) can be obtained by reacting an aldehyde compound of formula (V) with a mercaptal S-oxide of formula (VI) in the presence of a strong base to form a novel thiophene or furan derivative of formula (II), neutralizing the strong base contained in the reaction mixture, and then treating the reaction mixture with water or an alcohol of formula (III) in the presence of a mineral acid catalyst.

Typical examples of the novel compounds of formula (II) and their preparation are given in Examples A-1 to A-16 hereinbelow.

EXAMPLE A-1

10.315 g of 2-thiophenealdehyde and 11.420 g of formaldehyde dimethyl mercaptal S-oxide (FAMSO) were dissolved in 50 ml. of tetrahydrofuran, and 3 ml. of a 40% methanol solution of trimethylbenzylammonium hydroxide was added. Then, the mixture was heated under reflux for 6 hours. Methylene chloride (100ml.) was added, and the mixture was washed with 3N sulfuric acid, and then dried with Glauber's salt. The dried product was distilled at reduced pressure to afford b 17.31 g of 1-methylsulfinyl-1-methylthio-2(thienyl-2') ethylene having a boiling point of 147 to 152° C/0.11–0.13 mmHg as a pale yellow oily substance in a yield of 86%. The product was re-distilled, and the purified product was analyzed. The results were as follows:

Boiling point 151° C/0.11 mmHg
$I_R$ (neat): 1055, 710 cm$^{-1}$
NMR (CDCl$_3$): δ2.35s (3H), 2.70s (3H), 7.05m (1H), 7.40m (2H), 7.86s (1H)
Calculated for $C_8H_{10}OS_3$: C, 44.00 H, 4.62 S, 44.06
Found: C 43.81; H 4.83; S 44.00

EXAMPLE A-2

1.091 g of 2-thiophenealdehyde and 1.350 g of formaldehyde dimethyl mercaptal S-oxide were dissolved in 15 ml. of tetrahydrofuran, and 1 ml. of a 40% methanol solution of trimethylbenzylammonium hydroxide. The mixture was heated under reflux for 4 hours. 70 ml. of merhylene chloride was added, and the mixture was washed with water and dried with Glauber's salt. the mixture was the concentrated at reduced pressure, and the residue was separated by column chromatography (silica gel; methylene chloride and ethyl acetate) to afford 1.920 g of 1-methylsulfinyl-1-methylthio-2-(thienyl-2') ethylene as a pale yellow oily substance in a yield of 90%.

EXAMPLE A-3

1.234 g of 2-thiophenealdehyde and 1.455 g of formaldehyde dimethyl mercaptal S-oxide were dissolved in 15 ml. of dioxane, and 1 ml. of a 40% methanol solution of trimethylbenzylammonium hydroxide was added. The mixture was heated under reflux for 4 hours. The reation product was treated in the same way as in Example A-2 to afford 2.007 g of 1-methylsulfinyl-1-methylthio-2-(thienyl-2') ethylene in a yield of 83%.

EXAMPE A-4

The procedure of Example A-3 was repeated except that 2.903 g of formaldehyde diphenyl mercaptal S-oxide was used instead of 1.455 g of formaldehyde dimethyl mercaptal S-oxide. 2.649 g of 1-phenylsulfinyl-1-phenylthio-2-(thienyl-2') ethylene was obtained in a yield of 83%. The results of analyses were as follows:

IR (neat): 1048 cm$^{-1}$
NMR (CDCl$_3$): δ6.9 –7.5m (6H), 7.09s (5H), 7.6 –7.75m (2H), 8.32s (1H).

EXAMPLE A-5

The procedure of Example A-3 repeated except that 2.107 g of formaldehyde diisopropyl mercaptal S-oxide was used instead of 1.455 g of formaldehyde dimethyl mercaptal S-oxide. 1.975 g of 1-isoprpyl sulfinyl-1-isopropylthio-2-(thienyl-2') ethylene was obtained in a yield of 77%. The results of analyses were as follows:

m.p. 79°–80° C. (the sample was recrystallized from n-hexane)
IR (KBr): 1052 cm$^{-1}$
NMR (CDCl$_3$): δ1.03d(3H, H=7Hz), 1.30d (3H, J=7Hz), 3H, J=7Hz), 1.40d (3H, J=7Hz), 3.17 septet (1H, J=7Hz), 3.38 septet (1H, J=7Hz), 6.9–7.1m (1H), 7.3–7.45m (2H), 7.7s (1H)
For $C_{12}H_{18}OS_3$
Calculated: C. 52,51 H, 6.61 S, 35. 05
Found: C, 52.73 H, 6.64 S, 34.91

EXAMPLE A-6

1.043 g of 2-thiophenealdehyde and 1.221 g of formaldehyde dimethyl mercaptal S-oxide were dissolved in 15 ml. of methanol, and 440 mg of potassium hydroxide was added. The mixture was heated under reflux for 24 hours, and concentrated at reduced presssure. To the residue was added methylene chloride, and the insoluble matter was separated by filtration. The filtrate was concentrated at reduced pressure, and the residue was separated by column chromatography (silica gel; methylene chloride and ethyl acetate) to afford 1.689 g of 1-methylsulfinyl-1=methylthio-2(thienyl-2') ethylene in a yield of 83%.

EXAMPLE A-7

The procedure of Example A-6 was repeated except that 440 mg of sodium hydroxide and 15 ml. of ethanol were used instead of 440 mg of potassium hydroxide and 15 ml. of methanol. 1.491 g of 1-methylsulfinyl-1-methylthio-2-(thienyl-2') ethylene was obtained in a yield of 73%.

EXAMPLE A-8

1.231 g of 2-thiophenealdehyde and 1.370 g of formaldehyde dimethyl mercaptal S-oxide were added to a mixture of 9 ml. of ethanol and 1 ml. of water. 1.600 g of potassium carbonate was added, and the mixture was heated under reflux for 40 hours. The reaction mixture was concentrated at reduced pressure, and then 100 ml. of methylene chloride was added. The insoluble matter was separated by filtration. The filtrate was concentrated at reduced pressure, and separated by column chromatography (silica gel; melthylene chloride and ethyl acetate) to afford 0.971 g of 1-methylsulfinyl-1-methylthio-2-(thienyl-2')ethylene in a yield of 41%.

EXAMPLE A-9

1.425 g of 2-thiophenealdehyde and 1.595 g of formaldehyde dimethyl mercaptal S-oxide were added to an ethanol solution of sodium ethoxide (prepared from 0.35 g of metallic sodium and 15 ml. of ethanol), and the mixture was heated under reflux for 5 hours. The reaction product was treated in the same way as in Example A-6 to afford 2.318 g of 1-methylsulfinyl-1-methylthio-2-(thienyl-2') ethylene in a yield of 84%.

EXAMPLE A-10

2.115 g of 2-thiophenealdehyde and 2.836 g of formaldehyde diethyl mercaptal S-oxide were dissolved in 30 ml. of tetrahydrofuran, and 2 ml. of a 40% methanol solution of trimethylbenzylammonium hydroxide was added. The mixture was heated under reflux for 20 hours. The reaction was shaken with the addition of 100 ml. of methylene chloride and 30 ml. of 3N sulfuric acid. Then, the organic phase was separated. It was dried with Glauber's salt, and concentrated at reduced pressure. The residue was separated by column chromatography (silica gel; methylene chloride) to afford 3.803 g of 1-ethylsulfinyl-1-ethylthio-2(thienyl-2') ethylene as a yellow oily substance in yield of 89%. The results of analyses were as follows:

IR (neat): 1060 cm$^{-1}$
NMR (CDCl$_3$): δ1.20t (3H, J=8Hz), 1.28t (3H, J=8Hz), 2.54–3.14m (4H), 7.01 $d \times d$ (1H, J=4 and 6Hz), 7.28–7.36m (2H), 7.81s (1H)

EXAMPLE A-11

18.75 g of 3-thiophenealdehyde and 20.76 g of formaldehyde dimethyl mercaptal S-oxide were dissolved in 150 ml. of dioxane, and 30 ml. of a 40% methanol solution of trimethylbenzylammonium hydroxide was added. The mixture was heated under reflux for 45.5 hours. 150 ml. of melthylene chloride and 50 ml. of 3N sulfuric acid were added, and the mixture was shaken to separate the organic phase. The aqueous phase was extracted three times with 50 ml. of methylene chloride each time. The organic phase was combined with the extract, and the mixture was washed with a saturated aqueous solution of sodium bicarbonate. The organic phase was dried with Glauber's salt, and concentrated at reduced pressure. The residue was distilled at reduced pressure to afford 17.766 g of 1-methylsulfinyl-1-methylthio-2-(thienyl-3') ethylene having a boiling point of 158° to 162° C. as a pale yellow oily substance.

NMR (CDCl$_3$): δ2.30s (3H), 2.69s (3H), 7.62s (1H), 7.20–7.35m (1H), 7.56–7.93m (2H)
IR (neat): 1063 cm$^{-1}$
For C$_8$H$_{10}$OS$_3$
Calculated: C, 44.00 H, 4.62
Found: C, 44.37 H, 4.46

EXAMPLE A-12

1.573 g of 3-thiophenealdehyde and 1.820 g of formaldehyde dimethyl mercaptal S-oxide were dissolved in 15 ml. of dioxane, and a 40% methanol solution of trimethylbenzylammonium hydroxide was added. The mixture was heated under reflux for 21 hours, and treated in the same way as in Example A-10 to afford 2.014 g of 1-methylsulfinyl-1-methylthio-(thienyl-3') ethylene as a pale yellow oily substance in a yield of 66%.

EXAMPLE A-13

23.42 g of furfural and 29.00 g of formaldehyde dimelthyl mercaptal S-oxide were dissolved in 200 ml. of tetrahydrofuran, and 20 ml. of a 40% methanol solution of trimethylbenzylammonium hydroxide was added. The mixture was heated under reflux for 13.5 hours. 50 ml. of water and 20 ml. of 3N dilute sulfuric acid were added, and the mixture was extracted three times with 300 ml. of methylene chloride each time. The organic phase was dried with potassium carbonate and sodium sulfate (anhydrous), and concentrated at reduced pressure. The residue was distilled at reduced pressure to afford 33.53 g of 1 -methylsulfinyl-1-methylthio-2-(furyl-2') ethylene having a boiling point of 129° to 135° C. as a pale yellow oily substance in a yield of 71%.

Samples for analyses were obtained by purifying the product by re-distillation.

IR (neat): 1058 cm$^{-1}$
NMR (CDCl$_2$): δ2.35s (3H), 2.69s (3H), 6.48q (1H, J=2 and 4Hz), 7.05 $d \times d$ (1H, H=4Hz), 7.51 d (1H, H=2Hz), 7.51s(2H).
For C$_8$H$_{10}$O$_2$S$_2$
Calculated: C, 47.50 H, 4.98
Found: C, 47.62 H, 4.96

EXAMPLE A-14

1.110 g of furfural and 1.335 g of formaldelhyde dimethyl mercaptal S-oxide were dissolved in 20 ml. of methanol, and 750 mg. of potassium hydroxide was added. The mixture was heated under reflux for 43 hours, and concentrated at reduced pressure. 100 ml. of methylene chloride was added to the residue, and the insoluble matter was separated by filtration. The filtrate was concentrated at reduced pressure, and separated by column chromatography (silica gel; methylene chloride and ethyl acetate) to afford 1.049 g of 1-methylsulfinyl-1-methylthio-2-(furyl-2') ethylene as a yellow oily substance in a yield of 48%. The product was identified by NMR.

EXAMPLE A-15

27.63 g of 5-methyl-2-furfural and 29.00 g of formaldehyde dimethyl mercaptal S-oxide were dissolved in 300 ml. of tetrahydrofuran, and 20 ml. of a 40% methanol solution of trimethylbenzylammonium hydroxide was added. The mixture was heated under reflux for 43 hours. 300 ml. of methylene chloride was added to the reaction mixture, followed by washing two times with 60 ml. of 2N sulfuric acid each time. The washed product was dried with anhydrous potassium carbonate, and concentrated at reduced pressure. The residue was distilled at reduced pressure to afford 11.344 g of a pale yellow oily substance having a boiling point of 145 to 150° C./0.22 mmHg. This product was found to be 1-methylsulfinyl-1-methylthio-2-(5'-methylfuryl-2') ethylene from the following data.

IR (neat): 1060 cm$^{-1}$
NMR (CDCl$_3$): δ2.33s (6H), 2.66s(3H), 6.09d (1H, J=3.5Hz), 6.95d (1H, J=3.5 Hz), 7.42s (1H)
For C$_9$H$_{12}$O$_2$S$_2$
Calculated: C, 49.97 H, 5.59 Found: C, 50.35 H, 5.58

EXAMPLE A-16

1.085 g of furfural and 2.034 g of formaldelhyde diisopropyl mercaptal S-oxide were dissolved in 25 ml. of tetrahydrofuran, and 2 ml. of a 40% methanol solution of trimethylbenzylammonium hydroxide was added. The mixture was heated under reflux for 21 hours. 80 ml. of methylene chloride and 21 ml. of 3N sulfuric acid was added. The mixture was stirred for some time, and the organic phase was separated. The aqueous phase was extracted twice with 20 ml. of methylene chloride each time. The extract was combined with the organic phase, and the mixture was dried with anhydrous potassium carbonate. It was then concentrated at reduced pressure, and the residue was separated by column chromatography (silica gel; methylene chloride and ethyl acetate) to afford 1.525 g of 1-isopropylsulfinyl-1-isopropylthio-2-(furyl-2') ethylene as yellow crystals having a melting point of 53.5° to 54° C. The results of analyses were as follows:

IR (KBr): 1146, 1055, 1016, 770 cm$^{-1}$
NMR (CDCl$_3$): δ1.01d (3H, J=7Hz), 1.28d (6H, J=7Hz), 1.39d (3H, J=7Hz), 3.15 septet (1H, J=7Hz), 3.40 septet (1H, J=7Hz), 6.43 $d \times d$ (1H, J=4 and 2Hz), 7.08d (1H, J=4Hz), 7.45s (1H, 7.46d (1H, J=2Hz)

EXAMPLE B-1

533 mg of 1-methylsulfinyl-1-methylthio-2-(thienyl-2') ethylene was dissolved in 9 ml. of ethanol, and 1 ml. of ethanol saturated with hydrogen chloride was added. The mixture was stirred at room temperature for 22 hours. 10 ml. of ether was added, and after washing with water, the mixture was dried with Glauber's salt. It was concentrated at reduced pressure, and the residue was separated by column chromatography (silica gel; n-hexane and benzene) to afford 214 mg of ethyl 2-thienylacetate as a pale yellow liquid in a yield of 52%. The product was identified by NMR and IR.

EXAMPLE B-2

1.347 g of 1-methylsulfinyl-1-methylthio-2-(thienyl-2') ethylene was dissolved in 25 ml. of methanol, and 1.25 ml. of methanol saturated with hydrogen chloride gas was added. The mixture was stirred at room temperature for 16.5 hours and the same work-up as in Example B-1 afforded 283 mg of methyl 2-thienylacetate in a yield of 29%.

EXAMPLE B-3

872 of 1-methylsulfinyl-1-methylthio-2-(thienyl-2') ethylene was dissolved in 10 ml. of ethanol, and 1 ml. of ethanol saturated with hydrogen chloride was added under ice cooling. The mixture was stirred under ice cooling for 2 hours and then at room temperature for 66 hours, and concentrated at reduced pressure. The residue was separated by column chromatography (silica gel; n-hexane and benzene) to obtain 544 mg of ethyl 2-thienylacetate as a pale yellow oil in a yield of 80%.

EXAMPLE B-4

818 mg of 1-methylsulfinyl-1-methylthio-2-(thienyl-2') ethylene was added to 10 ml. of 24% hydrobromic acid, and the mixture was heated under reflux for 7 hours. The mixture was extracted thrice with 50 ml. of ether each time. The organic phase was dried with Glauber's salt, and concentrated at reduced pressure. The residue was separated by column chromatography (silica gel; benzene, methylene chloride and ethyl acetate) to afford 383 mg of a black brown oily product. A portion of the product which was soluble in 30 ml. of hot cyclohexane was separated by filtration, and the filtrate was treated with active charcoal, followed by concentration at reduced pressure to afford 325 mg of 2-thienylacetic acid in a yield of 61%.

EXAMPLE B-5

806 mg of 1-methylsulfinyl-1-methylthio-2-(thienyl-2')ethylene was dissolved in 10 ml. of methanol, and 10 ml. of 24% hydrobromic acid was added. The mixture was heated under reflux for 3 hours. The reaction mixture was extracted twice with 50 ml. of ether each time. The organic phase was dried with Glauber's salt and concentrated at reduced pressure. The residue was separated by column chromatography (silica gel; n-hexane and benzene) to afford 368 mg of methyl 2-thienylacetate in a yield of 64%.

EXAMPLE B-6

1.153 g of 1-methylsulfinyl-1-methylthio-2-(thienyl-2')ethylene was dissolved in 10 ml. of ethanol, and 0.3 ml. of ethanol saturated with hydrogen bromide was added. The mixture was stirred at 50° C. for 2.5 hours, and then heated under reflux for 45 minutes. After concentration at reduced pressure, the residue was separated by column chromatography (silica gel; n-hexane and benzene) to afford 746 mg of a pale yellow oily substance which was found by NMR to contain 663 mg of ethyl 2-thienylacetate. The yield was 74%.

EXAMPLE B-7

The procedure of Example B-6 was repeated except that 1.421 g of 1-isopropylsulfinyl-1-isopropylthio-2-(thienyl-2')ethylene was used instead of 1.153 g of 1-methylsulfinyl-1-methylthio-2-(thienyl-2')ethylene. 652 mg of ethyl 2-thienylacetate was formed in a yield of 74%.

EXAMPLE B-8

The procedure of Example B-6 was repeated except that 1.325 g of 1-phenylsulfinyl-1-phenylthio-2-(thienyl-2')ethylene was used instead of 1.153 g of 1-methylsulfinyl-1-methylthio-2-(thienyl-2')ethylene. 491 mg of ethyl 2-thienylacetate was formed in a yield of 75%.

EXAMPLE B-9

1.131 g of 1-methylsulfinyl-1-methylthio-2-(thienyl-2')ethylene was dissolved in 10 ml. of n-butanol, and 0.3 ml. of n-butanol saturated with hydrogen bromide was added. The mixture was stirred at 50° C. for 15 hours, and concentrated at reduced pressure. The residue was separated by column chromatography (silica gel; n-hexane and benzene) to afford 721 mg of n-butyl 2-thienylacetate in a yield of 70%.

EXAMPLE B-10

1.012 g of 1-methylsulfinyl-1-methylthio-2-(thienyl-3')ethylene was dissolved in 10 ml. of methanol, and 0.3 ml. of methanol saturated with hydrogen chloride was added. The mixture was heated under reflux for 19 hours, and then concentrated at reduced pressure. The residue was separated by column chromatography (silica gel; bezene) to afford 639 mg of methyl 3-thienylacetate in a yield of 88%.

EXAMPLE B-11

1.30 g of 1-methylsulfinyl-1-methylthio-2-(furyl-2')ethylene was dissolved in 10 ml. of methanol, and 0.2 ml. of methanol saturated with hydrogen chloride gas was added. The mixture was stirred at room temperature for 3 days, and then at 55° C. for 67 hours. The mixture was concentrated at reduced pressure, and the residue was separated by column chromatography (silica gel; methylene chloride) to afford 447 mg of methyl 2-furylacetate as a pale yellow liquid in a yield of 49%.

IR (neat): 1745 cm$^{-1}$

NMR (CDCl$_3$): $\delta$3.63s (2H), 3.66s (3H), 6.1–6.3m (2H), 7.31m (1H)

EXAMPLE B-12

1.385 g of 1-methylsulfinyl-1-methylthio-2-(furyl-2')ethylene was dissolved in 15 ml. of ethanol, and 0.1 ml. of conc. hydrobromic acid (more than 47%, specific gravity about 1.48) was added. The mixture was heated under reflux for 22 hours, and concentrated at reduced pressure. The residue was separated by column chromatography (silica gel; methylene chloride) to afford 570 mg of a yellow oily product which was found by NMR to contain 474 mg of ethyl 2-furylacetate and 96 mg of 2-furylacetic acid methanethiol ester. The yields of the products were 45%, and 9% respectively.

NMR of ethyl 2-furylacetate (CDCl$_3$): $\delta$1.26t (3H, J=7Hz), 3.67s (2H), 4.18q (2H, J=7Hz), 6.1–6.4m (2H), 7.35m (1H).

NMR of 2-furylacetic acid methane thiolester (CDCl$_3$):

$\delta$2.30s (3H), 3.87z (2H), 6.1–6.4m (2H), 7.35m (1H)

EXAMPLE B-13

1.217 g of 1-methylsulfinyl-1-methylthio-2-(furyl-2')ethylene was dissolved in 15 ml. of ethanol, and 0.2 ml. of ethanol saturated with hydrogen bromide was added. The mixture was heated under reflux for 23.5 hours. Furthermore, 0.2 ml. of ethanol saturated with hydrogen bromide was added, and the mixture was heated under reflux for 8 hours. After concentration at reduced pressure, the residue was separated by column chromatography (silica gel; methylene chloride) to afford 629 mg of an orange oily substance which was found by NMR to contain 540 mg of ethyl 2-furylacetate and 89 mg of 2-furylacetic acid methane thiol ester. The yields of these products were 58% and 10%, respectively.

EXAMPLE B-14

2.04 g of 1-methylsulfinyl-1-methylthio-2-(5'-methylfuryl-2')ethylene was dissolved in 20 ml. of methanol, and 0.3 ml. of methanol saturated with hydrogen chloride was added. The mixture was heated under reflux with stirring at 45° C. for 44 hours, and concentrated at reduced pressure. The residue was separated by column chromatography (silica gel; methylene chloride) to afford 381 mg of methyl 5-methyl-2-furylacetate and 240 mg of 5-methyl-2-furylacetic acid methanethiol ester.

Methyl 5-methyl-2-furylacetate

NMR (CDCl$_3$): $\delta$2.21s (3H), 3.56s (2H), 3.64s (3H), 5.82 diffused d (1H, J=3Hz), 6.01d (1H, J=3Hz)

IR (neat): 1745 cm$^{-1}$

5-Methyl-2-furylacetic acid methanethiol ester

NMR (CDCl$_3$): $\delta$2.82s (6H), 3.81s (2H), 5.91 diffused d (1H, J=3Hz), 6.07d (1H, J=3Hz)

EXAMPLE B-15

1.027 g of 1-methylsulfinyl-1-methylthio-2-(thienyl-2')ethylene was dissolved in 10 ml. of ethanol, and 0.3 ml. of ethanol saturated with hydrogen bromide was added. The mixture was heated under reflux for 4 hours, and concentrated at reduced pressure. To the residue were added 10 ml. of methanol and 400 mg of potassium hydroxide, and the mixture was heated under reflux for 2 hours. 30 ml. of water was added, and the mixture acidified with conc. hydrochloric acid. Then, the mixture was extracted thrice with 50 ml. of ether each time. The organic phase was dried with Glauber's salt, and concentrated at reduced pressure. The residue was separated by column chromatography (silica gel; benzene, methylene chloride and ethyl acetate) to afford 593 mg of colorless crystals which were found by NMR to contain 526 mg of 2-thienylacetic acid. The yield was 79%. By recrystallizing this product from benzene-n-hexane, substantially pure 2-thienylacetic acid (melting point 60° to 62° C.) was obtained.

EXAMPLE B-16

1.325 g of 1-methylsulfinyl-1-methylthio-2-(thienyl-2')ethylene was dissolved in 10 ml. of methanol, and 0.3 ml. of methanol saturated with hydrogen bromide was added. The mixture was heated under reflux for 8 hours. The reaction mixture was treated in the same way as in Example B-15 to afford 671 mg of 2-thienylacetic acid in a yield of 78%.

EXAMPLE B-17

The procedure of Example B-15 was repeated except that 1.402 g of 1-isopropylsulfinyl-1-isopropylthio-2-(thienyl-2')ethylene and 400 mg of sodium hydroxide were used instead of 1.027 g of 1-methylsulfinyl-1-methylthio-2-(thienyl-2')ethylene and 400 mg of potassium hydroxide. 552 mg of 2-thienylacetic acid was formed in a yield of 76%.

EXAMPLE B-18

1.633 g of 1-phenylsulfinyl-1-phenylthio-2-(thienyl-2')ethylene was dissolved in 10 ml. of ethanol, and 0.3 ml. of ethanol saturated with hydrogen bromide was added. The mixture was heated for 5 hours under reflux, and concentrated at reduced pressure. To the residue were added 10 ml. of methanol, 1.00 g of potassium carbonate and 1 ml. of water, and the mixture was heated under reflux for 3 hours. The reaction mixture was treated in the same way as in Example B-15 to afford 572 mg of 2-thienylacetic acid in a yield of 84%.

What we claim is:

1. A compound of the formula

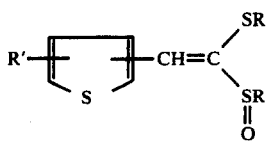

wherein R' represents a member selected from the group of hydrogen and alkyl and R represents a member selected from the group of (1) alkyl, (2) substituted alkyl wherein the substituent is halogen, hydroxy or alkoxy, (3) phenyl, and (4) substituted phenyl wherein the substituent is alkyl, alkoxy, aryl, nitro or halogen.

2. A compound according to claim 1 wherein R' is hydrogen or alkyl of 1 to 4 carbon atoms and R is alkyl of 1 to 5 carbon atoms or phenyl.

3. A compound according to claim 1, said compound being 1-methylsulfinyl-1-methylthio-2-(thienyl-2')ethylene.

4. A compound according to claim 1, said compound being 1-phenylsulfinyl-1-phenylthio-2-(thienyl-2')ethylene.

5. A compound according to claim 1, said compound being 1-isopropylsulfinyl-1-isopropylthio-2-(thienyl-2')ethylene.

6. A compound according to claim 1, said compound being 1-ethylsulfinyl-1-ethylthio-2-(thienyl-2')ethylene.

7. A compound according to claim 1, said compound being 1-methylsulfinyl-1-methylthio-2-(thienyl-3')ethylene.

* * * * *